United States Patent [19]

Camenzind

[11] Patent Number: 4,925,580

[45] Date of Patent: May 15, 1990

[54] THIADIAZOLE DERIVATIVES AS LUBRICANT ADDITIVES

[75] Inventor: Hugo Camenzind, Fribourg, Switzerland

[73] Assignee: Ciba-Geigy Corporation, Ardsley, N.Y.

[21] Appl. No.: 284,569

[22] Filed: Dec. 15, 1988

[30] Foreign Application Priority Data

Dec. 23, 1987 [CH] Switzerland ............ 5033/87

[51] Int. Cl.$^5$ .............. C10M 133/38; C10M 135/36
[52] U.S. Cl. ........................ 252/47; 252/47.5; 252/78.1; 548/142
[58] Field of Search ............ 548/142; 252/47, 47.5, 252/78.1

[56] References Cited

U.S. PATENT DOCUMENTS

| | | | |
|---|---|---|---|
| 2,331,749 | 10/1943 | Watt | 548/142 |
| 2,765,289 | 10/1956 | Fields et al. | 252/32.7 |
| 2,799,651 | 7/1957 | Richardson et al. | |
| 4,246,126 | 1/1981 | Arakelian et al. | 548/142 |
| 4,617,136 | 10/1986 | Doe, Jr. | 548/142 |
| 4,704,426 | 11/1987 | Doe, Jr. | 548/142 |

FOREIGN PATENT DOCUMENTS 275449  7/1988  European Pat. Off. ............ 548/142

OTHER PUBLICATIONS

J. Kobe et al., Croatica Chemica Acta 37 (1965), pp. 215-221.

*Primary Examiner*—William R. Dixon, Jr.
*Assistant Examiner*—Ellen M. McAvoy
*Attorney, Agent, or Firm*—Stephen V. O'Brien

[57] ABSTRACT

A lubricant composition or hydraulic oil composition containing at least one lubricant or one hydraulic oil and at least one 2,5-dimercapto-1,3,4-thiadiazole of general formula I

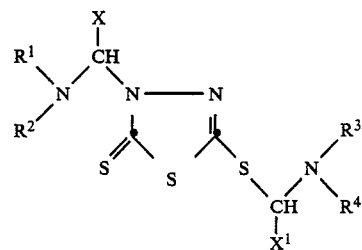

wherein $R^1$, $R^2$, $R^3$ and $R^4$, which are identical or different, are alkyl having 1 to 24 C atoms, alkenyl having 3 to 12 C atoms or phenyl-($C_1$-$C_4$)-alkyl which is unsubstituted or substituted in the phenyl radical by $C_1$-$C_4$-alkyl, or $R^1$ and $R^2$ and/or $R^3$ and $R^4$, with the N atom to which they are bonded, are a morpholine, piperidine, pyrrolidine, piperazine, methylpiperazine or perhydroazepine radical which is unsubstituted or substituted by $C_1$-$C_4$-alkyl, and X and $X^1$, which are identical or different, are H, alkyl having 1 to 23 C atoms, phenyl, phenyl-($C_1$-$C_4$)-alkyl or phenyl substituted by $C_1$-$C_{12}$-alkyl, $C_1$-$C_{12}$-alkoxy, hydroxyl, di($C_1$-$C_4$-alkyl)amino, halogen and/or nitro.

20 Claims, No Drawings

THIADIAZOLE DERIVATIVES AS LUBRICANT ADDITIVES

The present invention relates to compositions containing 2,5-dimercapto-1,3,4-thiadiazoles, to their use as lubricant additives or as additives in hydraulic oils, and to novel 2,5-dimercapto-1,3,4-thiadiazoles.

In the field of lubricant additives, attention is being increasingly directed to phosphorus-free and ashless additives.

U.S. Pat. No. 2 765 289 discloses 2,5-dimercapto-1,3,4-thiadiazoles substituted in the 2- and 5-positions by an alkyldiarylaminomethyl group. These compounds are proposed as corrosion inhibitors in lubricating oils. However, these products did not prove universally satisfactory. Thus the protection from abrasion and, in particular, the neutralization of active sulfur, corrosive to copper and silver, were unsatisfactory.

A Mannich reaction on 2,5-dimercapto-1,3,4-thiadiazole is known from J. Kobe, A. Pollak, A. Stanovnik and M. Tisler, Croatic Chemica Acta 37 (1965), pages 215-221, which describes 2,5-dimercapto-1,3,4-thiadiazole substituted in the 2- and 4-positions, for example by an N-morpholinomethyl radical.

It has now been found that, as well as being suitable antioxidants and anti-wear and extreme-pressure additives, certain 2,5-dimercapto-1,3,4-thiadiazoles which are both phosphorus-free and ashless are also capable of effectively protecting metal parts, including copper in particular, from corrosion and the corrosive effect of sulfur, i.e. they have a particularly broad polyvalent action as additives for lubricants or hydraulic oils.

The present invention accordingly relates to lubricant compositions or hydraulic oil compositions containing at least one lubricant or one hydraulic oil and at least one 2,5-dimercapto-1,3,4-thiadiazole of the general formula

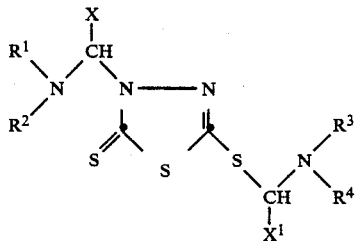
(I)

wherein $R^1$, $R^2$, $R^3$ and $R^4$, which are identical or different, are alkyl having 1 to 24 C atoms, alkenyl having 3 to 12 C atoms or phenyl-($C_1$-$C_4$)-alkyl which is unsubstituted or substituted in the phenyl radical by $C_1$-$C_4$-alkyl, or $R^1$ and $R^2$ and/or $R^3$ and $R^4$, with the N atom to which they are bonded, are a morpholine, piperidine, pyrrolidine, piperazine, methylpiperazine or perhydroazepine radical which is unsubstituted or substituted by $C_1$-$C_4$-alkyl, and X and $X^1$, which are identical or different, are H, alkyl having 1 to 23 C atoms, phenyl, phenyl-($C_1$-$C_4$)-alkyl or phenyl substituted by $C_1$-$C_{12}$-alkyl, $C_1$-$C_{12}$-alkoxy, hydroxyl, di($C_1$-$C_4$-alkyl)amino, halogen and/or nitro.

Alkyl having 1 to 24 C atoms comprises linear or branched alkyl groups including, for example, methyl, ethyl, propyl, isopropyl, n-butyl, isobutyl, 2-butyl, t-butyl, pentyl, isopentyl, hexyl, heptyl, 3-heptyl, n-octyl, 2-ethylhexyl, nonyl, decyl, undecyl, dodecyl, tridecyl, tetradecyl, pentadecyl, hexadecyl, heptadecyl, octadecyl or eicosyl.

By analogy, alkyl groups having 1 to 4 or 1 to 12 C atoms can be taken from the above list.

Examples of appropriate alkenyl substituents having 3 to 12 C atoms are allyl, 2-methallyl, but-2-enyl, hex-2-enyl, decenyl or 10-undecyl. Allyl is preferred.

Substituted or unsubstituted phenyl-($C_1$-$C_4$)-alkyl can be, for example, benzyl, α-methylbenzyl, α,α-dimethylbenzyl or t-butylbenzyl.

X and $X^1$ as alkyl having 1 to 23 C atoms, by analogy, the above examples apply, the methyl group being especially preferred.

Ethoxy, butoxy, t-butoxy, octoxy, 2-ethylhexyloxy etc. can be listed as examples of $C_1$-$C_{12}$-alkoxy.

Halogen is especially fluorine, chlorine or bromine and in particular chlorine.

An advantageous composition contains at least one compound of formula I wherein $R^1R^2$, $R^3$ and $R^4$ are $C_2$-$C_{18}$-alkyl or phenyl-($C_1$-$C_4$)-alkyl, or $R^1$ and $R^2$ and/or $R^3$ and $R^4$, together with the N atom to which they are bonded, are a morpholine, piperidine, piperazine or perhydroazepine radical which is unsubstituted or substituted by $C_1$-$C_4$-alkyl, and X and $X^1$ are H, alkyl having 1 to 10 C atoms, phenyl or phenyl substituted by —OH, in particular H.

Preferred compositions contain a compound of formula I wherein $R^1$, $R^2$, $R^3$ and/or $R^4$ can be an alkyl group having 2 to 18 C atoms or a phenylmethyl group.

Examples of preferred compositions are those in which $R^1$ and $R^3$ are identical and $R^2$ and $R^4$ are identical.

In other preferred compounds which can be contained in the composition, $R^1$ and $R^3$ are alkyl having 2-8 C atoms and $R^2$ and $R^4$ are phenylmethyl. A further possibility is for $R^1$, $R^2$, $R^3$ and $R^4$ to be identical and preferably to be 2-ethylhexyl or allyl in each case. In an advantageous form, the compositions contain compounds of formula I wherein X and $X^1$ are identical and are, in particular, H, alkyl having 1 to 10 C atoms, phenyl or phenyl substituted by —OH. X and $X^1$ will preferably be H.

The compounds of formula I can be prepared in a manner known per se. For example, 2,5-dimercapto-1,3,4-thiazole is first prepared by reacting one mol of hydrazine or a hydrazine salt with two mol of carbon disulfide in an alkaline medium, followed by acidification (U.S. Pat. No. 4 599 425). The compounds of formula I can be prepared from the 2,5-dimercapto-1,3,4-thiazole, for example according to the cited literature reference: Kobe et al., Croat. Chem. Acta 37 (1965) 215-221.

The process is carried out by bringing together the starting materials, i.e. the 2,5-dimercapto-1,3,4-thiadiazole, the appropriate amine and the appropriate aldehyde, and reacting them for periods of up to 24 h at temperatures which are not critical per se and are normally between room temperature and the reflux temperature, and advantageously at temperatures from 50° to 70° C. A solvent, in particular a non-polar solvent, is generally used, examples of possible solvents being carbon tetrachloride, aromatic and saturated aliphatic hydrocarbons, e.g. petroleum ethers, cyclohexane, methylcyclohexane, decalin, terpenes, benzene, toluene or xylenes, and suitable mixtures thereof.

To achieve optimum conversions and yields, the 2,5-dimercapto-1,3,4-thiadiazole, the aldehyde and the amine should be used in proportions of 1:3:3 to 1:2:2, the proportions 1:2:2 being preferable.

According to the desired end compound, the aldehydes can be taken from the series of the aliphatic or aromatic aldehydes having 1 to 24 C atoms and can be substituted by alkoxy, hydroxyl, mercapto and/or nitro groups. Example of specific aldehydes which can be used are formaldehyde, which is preferred, acetaldehyde, benzaldehyde, 2-ethylhexylaldehyde, butyraldehyde, oenanthaldehyde, capric aldehyde, salicylaldehyde and also, if appropriate, laurylaldehyde, acetylsalicylaldehyde, orthochlorobenzaldehyde, parachlorobenzaldehyde, cinnamaldehyde, parahydroxybenzaldehyde, octylaldehyde, decylaldehyde, p-methoxybenzaldehyde, phenylacetaldehyde or 2,5-dimethoxybenzaldehyde.

The amines which are also used can be dialkyl-, dialkenyl-, monoalkyl- monoarylalkyl- or diarylalkylamines, examples being di-n-butylamine, diisobutylamine, dihexylamine, dibenzylamine, benzylmethylamine, bis-2-ethylhexylamine, dioctylamine, diisooctylamine, diallylamine etc.; bis-2-ethylhexylamine and diallylamine are preferably used.

The following is a list of examples of especially preferred compounds which can also be obtained by the processes described, represent novel compounds and are particularly suitable for use in lubricant compositions: N,S-bis(dipropylaminomethyl)-2,5-dimercapto-1,3,4-thiadiazole, N,S-bis(dibutylaminomethyl)-2,5-dimercapto-1,3,4-thiadiazole, N,S-bis(dihexylaminomethyl)-2,5-dimercapto-1,3,4-thiadiazole, N,S-bis(benzylethylaminomethyl)-2,5-dimercapto-1,3,4-thiadiazole, N,S-bis[bis(2-ethylhexyl)aminoethyl]-2,5-dimercapto-1,3,4-thiadiazole, N,S-bis(dibenzylaminomethyl)-2,5-dimercapto-1,3,4-thiadiazole, N,S-bis(diallylaminomethyl)-2,5-dimercapto-1,3,4-thiadiazole, N,S-bis(ditridecylaminomethyl)-2,5-dimercapto-1,3,4-thiadiazole and N,S-bis(dioctadecylaminomethyl)-2,5-dimercapto-1,3,4-thiadiazole.

On account of their good solubility in oil, the compounds of the invention can be successfully used in lubricants in general and mineral oils and synthetic or semisynthetic oils in particular, acting as abrasion inhibitors or extreme pressure/antiwear additives (EP/AW), antioxidants (AO) and corrosion inhibitors (CI). The compounds are also suitable as additives for hydraulic oils. The compositions conventionally contain 0.01 to 10% by weight, advantageously 0.05 to 5% by weight and preferably 0.1 to 3% by weight of at least one compound of formula I according to the present invention, based in each case on the lubricant or hydraulic oil.

Suitable lubricants and hydraulic oils are familiar to those skilled in the art and are described e.g. in "Schmiermittel Taschenbuch" ("Handbook of Lubricants") (Hüthig Verlag, Heidelberg, 1974) and in "Ullmanns Encyclopädie der technischen Chemie" ("Ullmanns Encyclopaedia of Chemical Technology"), vol. 13, pages 85–94 (Verlag Chemie, Weinheim, 1977), or by D. Klamann in "Schmierstoffe und verwandte Produkte" ("Lubricants and Related Products"), Verlag Chemie, Weinheim (1982).

The lubricant can be, for example, an oil based on a mineral oil or a synthetic oil, or, if appropriate, a grease. The term mineral oil encompasses all mineral oils for lubrication purposes, such as mineral oils based on hydrocarbons. Synthetic oils can be, for example, aliphatic or aromatic carboxylic acid esters, polymeric esters, polyalkylene oxides, phosphoric acid esters, poly-α-olefins, silicones, glycols, polyglycols or polyalkylene glycols.

The lubricants or hydraulic oils may additionally contain other additives which are incorporated to enhance even further the basic properties of lubricants or of functional fluids in general; these additives include antioxidants, metal deactivators, rust inhibitors, viscosity index improvers, pour-point depressors, dispersants, surfactants and other extreme-pressure additives and anti-wear additives.

1. Alkylated monophenols 2,6-di-tert-butylphenol, 2,6-di-tert-butyl-4-methylphenol, 2,6-di-tert-butylphenol, 2-tert-butyl-4,6-dimethylphenol, 2,6-di-tert-butyl-3-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6,-tricyclohexylphenol, 2,6-di-tert-butyl-4-methoxymethylphenol, o-tert-butylphenol.

2. Alkylated hydroquinones 2,6-di-tert-butyl-4-methoxyphenol, 2,5-di-tert-butylhydroquinone, 2,5-di-tert-amylhydroquinone, 2,6-diphenyl-4-octadecyloxyphenol.

3. Hydroxylated thiodiphenyl ethers 2,2'-thio-bis(6-tert-butyl-4-methylphenol), 2,2'-thio-bis(4-octylphenol), 4,4'-thio-bis(6tert-butyl-3-methylphenol), 4,4'-thio-bis(6-tert-butyl-2-methylphenol).

4. Alkylidene-bisphenols 2,2'-methylene-bis(6-tert-butyl-4-methylphenol), 2,2'-methylene-bis(6-tert-butyl-4-ethylphenol), 2,2'-methylene-bis[4-methyl-6-(α-methylcyclohexyl)phenol], 2,2'-methylene-bis(4-methyl-6-cyclohexylphenol), 2,2'-methylene-bis(6-nonyl-4-methylphenol), 2,2'-methylene-bis(4,6-di-tert-butylphenol), 2,2'-ethylidene-bis(4,6-di-tert-butylphenol), 2,2'-ethylidene-bis(6-tert-butyl-4- or -5-isobutylphenol), 2,2'-methylene-bis[6-(α-methylbenzyl)-4-nonylphenol], 2,2'-methylene-bis[6-(α,α-dimethylbenzyl)-4-nonylphenol], 4,4'-methylene-bis(2,6-di-tert-butylphenol), 4,4'-methylene-bis(6-tert-butyl-2-methylphenol), 1,1-bis(5-tert-butyl-4-hydroxy-2-methylphenyl)butane, 2,6-di(3-tert-butyl-5-methyl-2-hydroxybenzyl)-4-methylphenol, 1,1,3-tris(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate.

5. Benzyl compounds 1,3,5-tri(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate.

6. Acylaminophenols 4-hydroxylauric anilide, 4-hydroxystearic anilide, 2,4-bis(octylmercapto)-6-(3,5-di-tert-butyl-4-hydroxyanilino)-s-triazine, octyl N-(3,5-di-tert-butyl-4-hydroxyphenyl)carbamate.

7. Esters of β-(3,5-di-tert-butyl-4-hydroxyphenyl)-propionic acid with monohydric or polyhydric alcohols, for example with methanol, diethylene glycol, octadecanol, triethylene glycol, hexane-1,6-diol, pentaerythritol, neopentyl glycol, tris(hydroxyethyl) isocyanurate, thiodiethylene glycol, bis(hydroxyethyl)oxalyldiamide.

8. Esters of β-(5-tert-butyl-4-hydroxy-3-methylphenyl)propionic acid with monohydric or polyhydric alcohols, for example with methanol, diethylene glycol, octadecanol, triethylene glycol, hexane-1,6-diol, pentaerythritol, neopentyl glycol, tris(hydroxyethyl) isocyanurate, thiodiethylene glycol, di(hydroxyethyl)oxalyldiamide.

9. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

Examples of amine antioxidants
N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di(naphth-2-yl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di(4-methoxyphenyl)-amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di[(2-methylphenyl)amino]ethane, 1,2-di(-phenylamino)propane, (o-tolyl)biguanide, di[4-(1',3'-dimethylbutyl)phenyl]amine, tert-octylated N-phenyl-1-naphthylamine, a mixture of monoalkylated and dialkylated tert-butyl- and tert-octyldiphenylamines, 2,3-dihydro-3,3-dimethyl-4H-1,4-benzothiazine, phenothiazine, N-allylphenothiazine.

Examples of further antioxidants aliphatic or aromatic phosphites, esters of thiodipropionic acid or thiodiacetic acid, or salts of dithiocarbamic or dithiophosphoric acid.

Examples of metal deactivators, e.g. for copper, are triazoles, benzotriazoles and derivatives thereof, toluotriazoles and derivatives thereof, 2-mercaptobenzothiazole, 2-mercaptobenzotriazole, 2,5-dimercaptobenzotriazole, 2,5-dimercaptobenzothiadiazole, 5,5'-methylene-bisbenzotriazole, 4,5,6,7-tetrahydrobenzotriazole, salicylidene-propylenediamine, salicylaminoguanidine and salts thereof.

Examples of rust inhibitors are
(a) organic acids and esters, metal salts and anhydrides thereof, e.g.: N-oleylsarcosine, sorbitan monooleate, lead naphthenate, alkenylsuccinic anhydrides, e.g. dodecenylsuccinic anhydride, partial esters and partial amides of alkenylsuccinic acids, 4-nonylphenoxyacetic acid.

(b) nitrogen-containing compounds, e.g.:
I. primary, secondary or tertiary aliphatic or cycloaliphatic amines and amine salts of organic and inorganic acids, e.g. oil-soluble alkylammonium carboxylates.
II. heterocyclic compounds, e.g.: substituted imidazolines and oxazolines.

(c) phosphorus-containing compounds, e.g.: amine salts of phosphoric acid partial esters or phosphonic acid partial esters, zinc dialkyldithiophosphates.

(d) sulfur-containing compounds, e.g.: barium dinonylnaphthalenesulfonates, calcium petroleumsulfonates.

Examples of viscosity index improvers are polyacrylates, polymethacrylates, vinylpyrrolidone/methacrylate copolymers, polyvinylpyrrolidones, polybutenes, olefin copolymers, styrene/acrylate copolymers, polyethers.

Examples of pour-point depressors are polymethacrylates, alkylated naphthalene derivatives.

Examples of dispersants/surfactants are polybutenylsuccinamides or polybutenylsuccinimides, polybutenylphosphonic acid derivatives, basic magnesium, calcium and barium sulfonates and phenates.

Examples of anti-wear additives are compounds containing sulfur and/or phosphorus and/or halogen, such as sulfurized vegetable oils, zinc dialkyldithiophosphates, tritolyl phosphate, chlorinated paraffins, alkyl and aryl disulfides and trisulfides, triphenyl phosphorothionates, diethanolaminoethyltolyltriazole, di(2-ethylhexyl)aminomethyltolyltriazole.

Finally, the lubricant composition can also contain a co-lubricant system containing conventional amounts of solid lubricants such as graphite, molybdenum disulfide, boron nitride or tetrafluoroethylene (Teflon).

The present invention also includes novel 2,5-dimercapto-1,3,4-thiadiazoles of general formula I

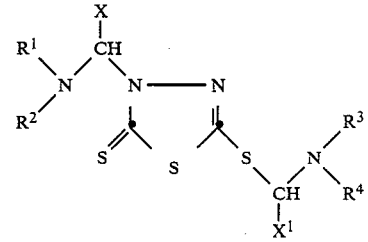

wherein $R^1$, $R^2$, $R^3$ and $R^4$, which are identical or different, are alkyl having 1 to 24 C atoms, alkenyl having 3 to 12 C atoms or phenyl-($C_1$–$C_4$)-alkyl which is unsubstituted or substituted by $C_1$–$C_4$-alkyl in the phenyl radical, or $R^1$ and $R^2$ and/or $R^3$ and $R^4$, with the N atom to which they are bonded, are a morpholine, piperidine, pyrrolidine, piperazine, methylpiperazine or perhydroazepine radical which is unsubstituted or substituted by $C_1$–$C_4$-alkyl, and X and $X^1$, which are identical or different, are H, alkyl having 1 to 23 C atoms, phenyl, phenyl-($C_1$–$C_4$)-alkyl or phenyl substituted by $C_1$–$C_{12}$-alkyl, $C_1$–$C_{12}$-alkoxy, hydroxyl, di-($C_1$–$C_4$)-alkylamino, halogen and/or nitro, with the proviso that $R^1$ and $R^2$, and $R^3$ and $R^4$, with the N atom to which they are respectively bonded, are not simultaneously a morpholino radical when X=H.

Preferred compounds of formula I are those in which $R^1$, $R^2$, $R^3$ and/or $R^4$ are an alkyl group having 2 to 18 C atoms or a phenylmethyl group, compounds of formula I in which $R^1$ and $R^3$ are identical and $R^2$ and $R^4$ are identical and as defined above, and also compounds of formula I in which $R^1$ and $R^3$ are alkyl having 2–8 C atoms and $R^2$ and $R^4$ are phenylmethyl.

Finally, especially preferred compounds of formula I are those in which $R^1$, $R^2$, $R^3$ and $R^4$ are identical and, in particular, are 2-ethylhexylamine in each case.

Further compounds of formula I which are included among the advantageous embodiments are those in which X and $X^1$ are identical and are H, alkyl having 1 to 10 C atoms, phenyl or phenyl substituted by —OH, preferred compounds of formula I being those in which X and $X^1$ are H.

By analogy, advantageous or preferred compounds are those which have general formula I and which lead to the advantageous or preferred compositions.

The present invention also includes a process of making a lubricant or a hydraulic fluid having improved extreme-pressure and anti-wear properties, improved antioxidant properties and improved corrosion properties, comprising the step of adding to said lubricant or hydraulic fluid an effective amount of a compound of the formula I as mentioned above.

The following Examples will serve to illustrate the present invention in greater detail. In these Examples and in the remaining description, parts and percentages are by weight, unless stated otherwise.

EXAMPLE 1

N,S-Bis(di-n-hexylaminomethyl)-2,5-dimercapto-1,3,4-thiadiazole

A suspension of 7.7 g (0.051 mol) of 2,5-dimercapto-1,3,4-thiadiazole and 9.6 g of aqueous formaldehyde (36%, 0.12 mol) is added to a solution of 18.9 g (0.1 mol) of di-n-hexylamine in 50 ml of toluene. The reaction mixture is stirred for approx. 15 hours at 50° C. The water is then separated from the organic phase. The latter is washed with water until neutral and evaporated, yielding 26 g of a reddish orange oil (95% of theory) which corresponds to the title compound.

The compounds of Examples 2–9 were prepared analogously. The compounds of Examples 1–9 have the general formula

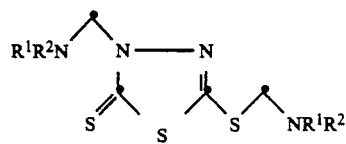

and the meanings of $NR^1R^2$ are given in the following Table.

| Example | $NR^1R^2$ | Yield (% of theory) | Appearance | $R^1R^2N\diagdown CH_2 \diagup N/S$ $^1$H-NMR [CDCl$_3$, ppm] | Analysis [calculated / found] C | H | N | S |
|---|---|---|---|---|---|---|---|---|
| 1 | di-n-hexylamine | 95 | reddish orange oil | 5.15 (2H, s) | 61.71 / 62.10 | 10.36 / 10.18 | 10.28 / 10.63 | 17.65 / 16.95 |
| 2 | di-n-propylamine | 58 | brown oil | 5.41 (2H, s) | 51.02 / 50.79 | 8.56 / 8.29 | 14.88 / 14.99 | 25.54 / 24.59 |
| 3 | di-n-butylamine | 88 | brown oil | 5.14 (2H, s) | 55.51 / 55.54 | 9.32 / 9.27 | 12.95 / 13.21 | 22.23 / 21.54 |
| 4 | ethylbenzylamine | 93 | brown oil | 5.11 (2H, s, broad) | — | — | — | — |
| 5 | dibenzylamine | 93 | yellowish orange high-viscosity oil | 5.01 (2H, 2 × s) | 67.57 / 66.93 | 5.67 / 5.57 | 9.85 / 10.41 | 16.91 / 17.19 |

-continued

| Example | NR$^1$R$^2$ | Yield (% of theory) | Appearance | R$^1$R$^2$N$\diagdown$CH$_2$$\diagdown$N/S $^1$H-NMR [CDCl$_3$, ppm] | Analysis [calculated / found] C | H | N | S |
| --- | --- | --- | --- | --- | --- | --- | --- | --- |
| 6 | di-2-ethylhexyl-amine | 96 | yellow oil | 5.13 (2H, s) | 65.80 | 11.04 | 8.53 | 14.64 |
|  |  |  |  |  | 65.79 | 11.17 | 8.77 | 14.18 |
| 7 | diallylamine | 90 | brown oil | 5.22 | 52.14 | 6.56 | 15.20 | 26.1 |
|  |  |  |  |  | 52.16 | 6.79 | 15.83 | 25.5 |
| 8 | ditridecylamine N(C$_{13}$H$_{27}$)$_2$ | 99 | orange oil | 5.14 | 71.73 | 12.04 | 5.98 | 10.26 |
|  |  |  |  |  | 73.44 | 12.45 | 5.79 | 8.5 |
| 9 | dioctadecylamine N(C$_{18}$H$_{37}$)$_2$ | 99 | yellow powder, m.p. 40–49° C. | 5.14 | 74.93 | 12.58 | 4.6 | 7.89 |
|  |  |  |  |  | 74.78 | 12.46 | 4.76 | 7.73 |

EXAMPLE 10

Test for anti-wear properties

The test for suitability as anti-wear additives is carried out by the ASTM standard method D-2783-81 using the Shell four-ball machine. Catenex ®P941 from Shell is used as the base oil. The mean wear scar diameter is measured under a load of 40 kg for 1 hour (in mm).

| Compound of Example | Amount of additive (% by weight) relative to base oil | WSD (mm) |
| --- | --- | --- |
| no additive | — | 0.9 |
| 6 | 1 | 0.55 |
| 7 | 1 | 0.64 |
| 8 | 1 | 0.53 |
| 9 | 1 | 0.50 |

EXAMPLE 11

Test for stabilization against oxidative degradation (TFOUT: Thin Film Oxygen Uptake test)

This test is a modified form of the rotary bomb test for mineral oils (ASTM D 2272). There is a detailed description by C. S. Ku and S. M. Hsu in Lubrication Engineering 40 (1984) 75–83. The test oil in this case is a commercial engine oil 15W40 with approx. half the conventional content of zinc dithiophosphates (0.75% of ZnDTP, 550 ppm of P, 1160 ppm of Zn). The additive to be tested is tested for its stabilizing action in the oil in the presence of water (2%), an oxidized/nitrated petroleum ether fraction (4%) and a mixture of liquid metal naphthenates (4%) under an oxygen pressure of 6.1 bar and at 160° C. The water and both the liquid catalysts for the test are obtained from the National Bureau of Standards (NBS) as Standard Reference Material 1817 with a certificate of analysis. The test is complete when a distinct kink in the pressure/time diagram indicates the onset of oxidation at the end of the induction period [min].

A long induction period means that the additive has a good stabilizing action.

| Compound of Example | Amount of additive (% by weight) relative to base oil | Induction period (min) |
| --- | --- | --- |
| no additive | — | 83 |
| 6 | 0.5 | 154 |
| 7 | 0.5 | 209 |
| 8 | 0.5 | 136 |
| 9 | 0.5 | 138 |

EXAMPLE 12

Test for protection of copper against corrosion by active sulfur

A brightly polished copper sheet of 60×10×1 mm is immersed in turbine oil containing 50 ppm of dissolved sulfur and 0.2% of the additive to be tested. The samples are heated at 100° C. for 2 hours. In a second step, the same copper sheets are rinsed with petroleum ether, put back into a turbine oil containing 50 ppm of active sulfur and heated at 100° C. for 24 hours. The colour of the sheets is assessed according to ASTM D 130 by comparison with a standard colour chart. There are 4 grades of assessment:

1—no tarnish
2—moderate tarnish
3—strong tarnish
4—corrosion

A and B denote a subdivision within the numerical groups 1 to 4 and relate to the formation of shadows on the samples. The evaluation A is superior to B in the qualitative assessment.

| Compound of Example | Additive (% by weight) relative to base oil | Colour 100° 2 hours | 100° 24 hours |
|---|---|---|---|
| no additive | — | 3 B | — |
| 6 | 0.2 | 1 A | 1 B |

What is claimed is:

1. A lubricant composition or hydraulic oil composition containing at least one lubricant or one hydraulic oil and at least one 2,5-dimercapto-1,3,4-thiadiazole of the general formula I

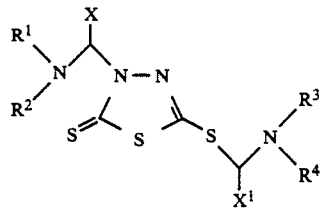

wherein $R^1$, $R^2$, $R^3$ and $R^4$, which are identical or different, are alkyl having 1 to 24 C atoms, alkenyl having 3 to 12 C atoms or phenyl-$(C_1-C_4)$-alkyl which is unsubstituted or substituted in the phenyl radical by $C_1-C_4$-alkyl and X and $X^1$, which are identical or different, are H, alkyl having 1 to 23 C atoms, phenyl, phenyl-$(C_1-C_4)$-alkyl or phenyl substituted by $C_1-C_{12}$-alkyl, $C_1-C_{12}$-alkoxy, hydroxyl, di($C_1-C_4$-alkyl)amino, halogen and/or nitro.

2. A composition according to claim 1 wherein $R^1$, $R^2$, $R^3$ and $R^4$ are $C_2-C_{18}$-alkyl or phenyl-$(C_1-C_4)$-alkyl and X and $X^1$ are H, alkyl having 1 to 10 C atoms, phenyl or phenyl substituted by —OH.

3. A composition according to claim 1 wherein $R^1$, $R^2$, $R^3$ and/or $R^4$ are an alkyl group having 2 to 18 C atoms, allyl or a phenylmethyl group.

4. A composition according to claim 1 wherein $R^1$ and $R^3$ are identical and $R^2$ and $R^4$ are identical and as defined above.

5. A composition according to claim 1 wherein $R^1$ and $R^3$ are alkyl having 2-8 C atoms and $R^2$ and $R^4$ are phenylmethyl.

6. A composition according to claim 1 wherein $R^1$, $R^2$, $R^3$ and $R^4$ are each 2-ethylhexyl.

7. A compositon according to claim 1 wherein X and $X^1$ are identical and are H, alkyl having 1 to 10 C atoms, phenyl or phenyl substituted by —OH.

8. A composition according to claim 1 wherein X and $X^1$ are H.

9. A composition according to claim 1 containing N,S-bis[bis(2-ethylhexyl)aminomethyl]-2,5-dimercapto-1,3,4-thiadiazole and/or N,S-bis(diallylaminomethyl)-2,5-dimercapto-1,3,4-thiadiazole.

10. A composition according to claim 1 containing 0.01 to 10% by weight, advantageously 0.05 to 5% by weight and preferably 0.1 to 3% by weight of at least one compound of formula I, based on the lubricant.

11. A 2,5-dimercapto-1,3,4-thiadiazole of general formula I

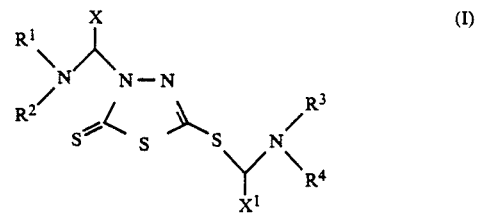

wherein $R^1$, $R^2$, $R^3$ and $R^4$, which are identical or different, are alkyl having 1 to 24 C atoms, alkenyl having 3 to 12 C atoms or phenyl-$(C_1-C_4)$-alkyl which is unsubstituted or substituted in the phenyl radical by $C_1-C_4$-alkyl and X and $X^1$, which are identical or different, are H, alkyl having 1 to 23 C atoms, phenyl, phenyl-$(C_1-C_4)$-alkyl or phenyl substituted by $C_1-C_{12}$-alkyl, $C_1-C_{12}$-alkoxy, hydroxyl, di($C_1-C_4$-alkyl)amino, halogen and/or nitro.

12. A compound of formula I according to claim 11 wherein $R^1$, $R^2$, $R^3$ and $R^4$ are $C_2-C_{18}$-alkyl or phenyl-$(C_1-C_4)$-alkyl and X and $X^1$ are H, alkyl having 1 to 10 C atoms, phenyl or phenyl substituted by —OH.

13. A compound of formula I according to claim 11 wherein $R^1$, $R^2$, $R^3$ and/or $R^6$ are an alkyl group having 2 to 18 C atoms or a phenylmethyl group.

14. A compound of formula I according to claim 11 wherein $R^1$ and $R^3$ are identical and $R^2$ and $R^4$ are identical and as defined above.

15. A compound of formula I according to claim 11 wherein $R^1$ and $R^3$ are alkyl having 2-8 C atoms and $R^2$ and $R^4$ are phenylmethyl.

16. A compound of formula I according to claim 11 wherein $R^1$, $R^2$, $R^3$ and $R^4$ are each 2-ethylhexyl.

17. A compound of formula I according to claim 11 wherein X and $X^1$ are identical and are H, alkyl having 1 to 10 C atoms, phenyl or phenyl substituted by —OH.

18. A compound of formula I according to claim 11 wherein X and $X^1$ are H.

19. The following compounds of formula I according to claim 11: N,S-bis[bis(2-ethylhexyl)aminomethyl]-2,5-dimercapto-1,3,4-thiadiazole and N,S-bis(diallylaminomethyl)-2,5-dimercapto-1,3,4-thiadiazole.

20. A process of making a lubricant or a hydraulic fluid having improved extreme-pressure and anti-wear properties, improved antioxidant properties and improved corrosion properties, comprising the step of adding to said lubricant or hydraulic fluid an effective amount of a compound of the formula I according to claim 1.

* * * * *